United States Patent [19]

King

[11] Patent Number: 5,188,601
[45] Date of Patent: Feb. 23, 1993

[54] DISPOSABLE SAFETY SYRINGE

[76] Inventor: Richard J. King, 113 Commodore Dr., Jupiter, Fla. 33477

[21] Appl. No.: 787,915

[22] Filed: Nov. 6, 1991

[51] Int. Cl.$^5$ ............................................. A61M 5/32
[52] U.S. Cl. .................................... 604/110; 604/195
[58] Field of Search ............... 604/110, 195, 187, 263, 604/218

[56] References Cited

U.S. PATENT DOCUMENTS

| | | |
|---|---|---|
| 2,888,923 | 11/1955 | Da Cunha Reis . |
| 3,584,626 | 6/1971 | Johansson . |
| 3,677,245 | 7/1972 | Welch . |
| 4,316,463 | 2/1982 | Schmitz et al. . |
| 4,507,117 | 3/1985 | Vining et al. ........................ 604/196 |
| 4,643,199 | 2/1987 | Jennings, Jr. et al. ............... 128/763 |
| 4,650,468 | 3/1987 | Jennings, Jr. ....................... 604/110 |
| 4,664,653 | 5/1987 | Sagstetter et al. .................. 604/197 |
| 4,675,005 | 6/1987 | Deluccia ............................. 604/110 |
| 4,692,156 | 9/1987 | Haller ................................. 604/195 |
| 4,915,699 | 4/1990 | Kornberg ............................ 604/195 |
| 4,969,877 | 11/1990 | Kornberg ............................ 604/195 |
| 4,986,813 | 1/1991 | Blake, III et al. ............... 604/195 X |
| 4,995,874 | 2/1991 | Strickland .......................... 604/195 |
| 5,030,208 | 7/1991 | Novacek et al. ............... 604/110 X |
| 5,049,136 | 9/1991 | Johnson ........................... 604/263 X |

Primary Examiner—John D. Yasko
Attorney, Agent, or Firm—Ernest V. Linek

[57] ABSTRACT

Disclosed is a syringe assembly which greatly reduces the chances of an operator coming in contact with an infectious needle. The syringe assembly is initially provided with its needle retracted within its barrel, in a sterile and safe environment. When used, the needle is engaged by the plunger, and locked in place at the forward end of the syringe barrel. Before disposal, the needle is withdrawn back into the barrel, and the plunger is broken off. Thus, the disposed of syringe is incapable of being reused, and there is little or no danger of accidental punctures, because the needle is retained within the syringe barrel.

17 Claims, 2 Drawing Sheets

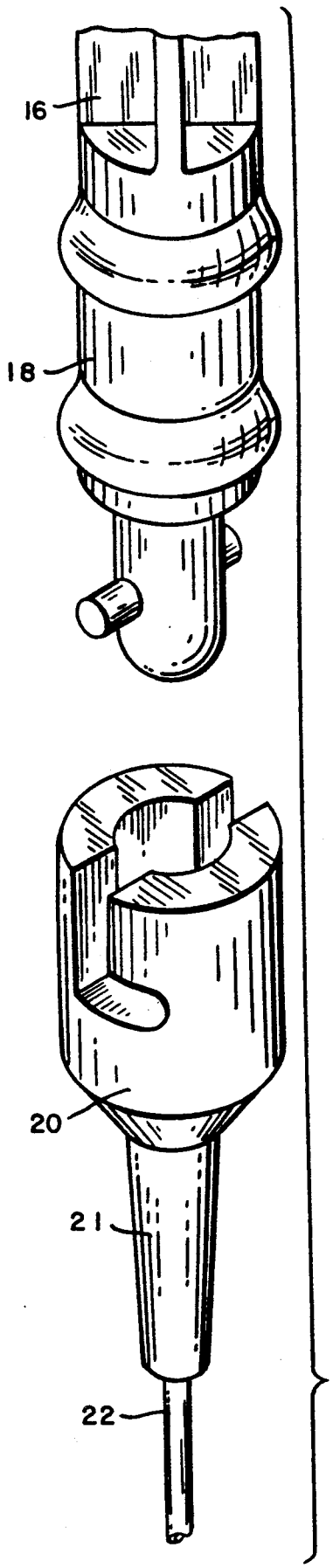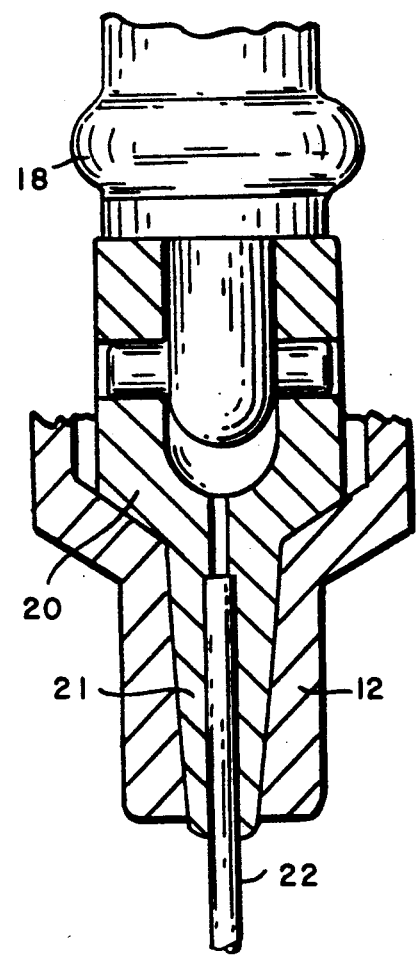
FIG. 6
FIG. 7

DISPOSABLE SAFETY SYRINGE

FIELD OF THE INVENTION

This invention relates to a disposable syringe which initially is provided with its needle retracted within its barrel, in a sterile and safe environment. When used, the needle is engaged by the plunger, and locked in place at the forward end of the syringe. Before disposal, the needle is withdrawn back into the barrel, and the plunger is broken off. Thus, the disposed of syringe is incapable of being reused, and there is little or no danger of accidental punctures, because the needle is retained within the syringe barrel.

BACKGROUND OF THE INVENTION

The concern over protecting medical personnel from coming into contact with infectious diseases by contact with contaminated syringe needles has led to the development of many syringes with retractable needles. The recent concern over the avoidance of being infected with the HIV (or AIDS) virus has led to even a greater importance being placed in the use of syringes incorporating retractable needles.

U.S. Pat. Nos. 4,650,468 and 4,643,199 are examples of syringes which have been developed so as to allow for a potentially infectious needle to be withdrawn into the syringe's interior after use. Both of theses patents utilize a somewhat complex mechanism to position the needle in an operational position and/or to retract the needle back into the syringe housing. The complexity of these designs can be a problem when quick positioning of the needle is essential, e.g., in an emergency situation.

U.S. Pat. Nos. 4,507,117 and 4,675,005 illustrate other syringe designs having retractable needles which are releasably connected directly to the plunger by way of rotation. As above, the complex mechanisms employed by these syringe designs can be a problem when quick positioning of the needle is essential, e.g., in an emergency situation.

U.S. Pat. No. 4,692,156 shows a retractable syringe needle which is locked directly onto the sealing plug of a plunger. In one embodiment, there is disclosed a snapping connection means between the needle and plug. Once this snapping connection has been made, it is essentially nondetachable and thus this invention represents a one shot device. In other words, any inadvertent attachment before use cannot be remedied.

Other syringes having safety features that have been designed to prevent accidental punctures and/or which prevent reuse are shown in the following patents:

U.S. Pat. No. 4,664,653 which describes a one step manually activated injection apparatus capable of injecting multiple premeasured dose of liquid medicaments without visibility of the needle.

U.S. Pat. No. 3,677,245 which discloses a self-contained disposable syringe including a syringe barrel with an open rear end and a needle mounted on the forward end. The needle has a passage therethrough which communicates with the interior of the barrel. A plunger is positioned within the syringe barrel and is movable with respect to the barrel.

U.S. Pat. No. 2,888,923 which describes a syringe for use with a sterile needle comprising a casing and a piston slidably engaged with said casing. The piston comprises a first hollow tube and a second hollow tube within and threadably engaging the first hollow tube. The second hollow tube is axially adjustable with respect to the first hollow tube and adapted for substantially complete insertion therein, whereby the piston length maybe controlled.

U.S. Pat. No. 3,584,626 which discloses a hypodermic syringe having a syringe body, a piston rod arranged movably in the body and an injection needle, in which the injection needle is housed inside the syringe body prior to the use of the syringe. When the needle is moved into its injection position, it is brought into a sealing abutment with a seating member arranged in the syringe body.

U.S. Pat. No. 4,316,463 which discloses a hypodermic injection device wherein the needle is initially isolated from a possibly corrosive medicament, but wherein the needle is movable to a position in flow communication with the medicament only at the moment of injection.

U.S. Pat. No. 4,969,877 discloses a syringe assembly which includes an outer casing within which an inner chamber slides. A plunger having a sealing plug at one end extends into both the inner chamber and outer casing such that the sealing plug is fixedly secured within the interior of the inner chamber and outer casing, yet is free to slide along the length of the inner chamber. The inner chamber and outer casings are structured such that the needle can be retracted completely within the interior of the outer casing when the inner chamber is releasably locked at the rear end of the outer casing. The needle can also be placed into an operational position when the inner chamber with attached needle is releasably locked at the forefront of the outer casing.

U.S. Pat. No. 4,915,699 describes a syringe assembly which includes an outer casing within which an inner chamber slides. A plunger having a sealing plug at one end extends into both the inner chamber and outer casing such that the sealing plug is fixedly secured within the interior of the inner chamber and outer casing, yet free to slide along the length of the inner chamber. The inner chamber and outer casing are structured such that the needle can be retracted completely within the interior of the outer casing when the inner chamber is releasably locked at the rear end of the outer casing.

SUMMARY OF THE INVENTION

The present invention provides a disposable hypodermic syringe wherein the needle is initially provided in a sterile and protected position, and where after an injection is given, the needle is again easily returned to the protective position for safe disposal.

One principal object of the present invention was to provide a simple design, having few moving parts, so that the syringe could be readily manufactured from inexpensive, but FDA acceptable materials that, due to their low cost, are deemed disposable, e.g., injection molded plastics. Another object of the present invention was to design a disposable syringe that would be useful as required, but which after use, would be nearly impossible to reuse, i.e., a one-time-only syringe.

These and other objects of the invention have been accomplished by designing the present syringe which consists of five simple components; (1) an injection molded syringe barrel with a constricted neck portion; (2) an injection molded plunger assembly, with (3) a rubber gasket located near the front end thereof (used to form the necessary vacuum) and the male locking portion of a ¼-turn "T" turn mechanism situated at its forward end; a needle assembly, consisting of (4) an injection molded hub including a ¼-turn "T" receptacle (i.e., female end) molded in place at the rearward end, and (5) a conventional syringe needle bonded to the forward end of the hub.

As sold, the syringe will have the needle assembly withdrawn into the barrel, with the plunger assembly either engaged or disengaged, (but preferably engaged). Advantageously, the forward tip of the syringe will include a thin segment of plastic or other sealing material so that the interior of the syringe can remain sterile until use.

To use the syringe of the present invention, the plunger assembly is inserted into the rear end of the needle assembly and this combination is pushed forward. The needle pierces the sealing material at the end of the barrel, and the forward tip of the needle assembly fits snugly and securely within the tip of the barrel. The two tip members are designed to provide a frictional interference or wedge fit which will withstand the force typically used during the injection process, but which, with a slight twisting motion on the plunger, can be disengaged when the syringe is to be disposed of.

Once the tips are locked, the syringe is filled with the injectable material by pulling back the plunger assembly an appropriate amount. The injection is made by inserting the needle as appropriate, and the plunger is depressed, injecting the contents. The plunger assembly is then used to reengage the needle assembly, using the ¼-turn "T" locking means, and the needle assembly locked on and then pulled back into the safety position, i.e., back into the syringe barrel. Advantageously, a score line is provided at the forward end of the plunger, and this score line becomes visible only after the needle has been fully retracted into the syringe barrel. Once the score line has been exposed, the plunger is snapped off, rendering the syringe incapable of reuse. The needle is safely housed within the barrel and the two pieces may be disposed of as required by law.

BRIEF DESCRIPTION OF THE DRAWINGS

FIG. 6 is a close up view of the disconnected male and female portions of the ¼-turn "T" locking mechanisms on the plunger and needle assemblies respectively.

FIG. 7 is a sectional view of the connected male and female portions of the ¼-turn "T" locking mechanisms on the plunger and needle assemblies, as well as the matched tip members of the barrel and needle assembly.

DETAILED DESCRIPTION OF THE PREFERRED EMBODIMENT

Figure 1:
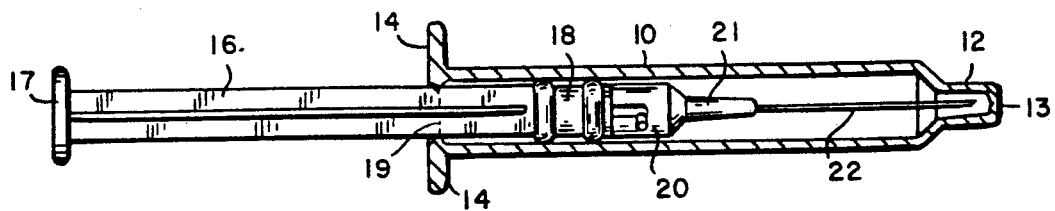
FIG. 1 is a partially cut away view of the syringe of the present invention, illustrating the needle in its "on-sale" mode, i.e., in a sterile condition.

Referring in detail to the drawings accompanying this disclosure, the present invention is directed to a disposable safety syringe. As illustrated in FIG. 1, the syringe of the present invention consists of an injection molded plastic barrel 10, which includes a tip portion 12, which, prior to use, is safety sealed at the end of the tip 13. The barrel is advantageously molded to include finger grips 14 at the back end.

As further illustrated in FIG. 1, the syringe of the present invention includes an injection molded plunger member 16, which includes a thumb pad 17 at its back end, and includes a separate rubber gasket 18 near its forward end. The rubber gasket 18 creates the necessary seal between the forward end of the plunger and the barrel of the syringe, so that the syringe will operate in a conventional manner. Finally, as illustrated, the plunger body 16 is provided with a score line 19, which allows the plunger to be easily broken off after use, rendering the syringe incapable of reuse.

Finally, as shown in FIG. 1, the syringe of the present invention includes a needle assembly consisting of an injection molded hub 20 which includes a tip member 21 and which terminates with a needle 22 at its forward end. The rear portion of hub 20 consists of a ¼-turn "T" receptacle, adapted to accept a corresponding male ¼-turn "T" member on the forward end of the plunger 16. These features will be more apparent in the later figure descriptions.

Figure 2:
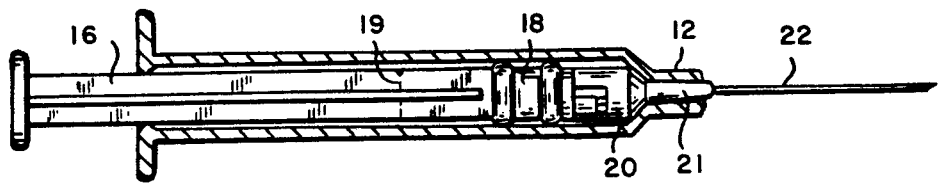
FIG. 2 is a partially cut away view of the syringe of the present invention, showing the positioning of the needle assembly and plunger when ready for use (or immediately after use).

As illustrated in FIG. 1, the very tip of the barrel 13 is injection molded to be closed by a thin plastic membrane, so that the needle can be kept in a sterile position. By pushing the plunger and the needle forward, the needle 22 will push through the plastic membrane 13, and the tip 21 of the needle assembly 20 will fit snugly within tip 12 of the syringe barrel. Plastic tip membrane 13 is advantageously made via a flash area in the mold so the wall of the membrane will have a breakthrough point to allow the needle to pass easily through it. As illustrated in FIG. 2, this allows the needle to come forward in its position to be useful for giving an injection.

As shown in FIG. 2, needle 22 has been pushed through tip 13, and now is located outside the syringe barrel 10, in a ready to use position. By careful design, the tip of the syringe barrel 12 and the tip of the needle assembly 21, have been matched in size to create a wedge fit between the two components.

The wedge fit between tips 12 and 21 is one of the necessary components that establish the tight fit for the syringe of the present invention to form a simple vacuum seal. The other vacuum seal component is rubber gasket 18, located near the forward end of plunger 16. Gasket 18 is designed to have a tight tolerance between the inside wall of the syringe barrel, and this tight, but flexible fit, allows the plunger to be easily moved back and forth inside the barrel, thereby enabling the syringe to draw and/or discharge liquids. The gasket is advantageously made of a soft synthetic rubberized material that is FDA approved.

Figure 3:
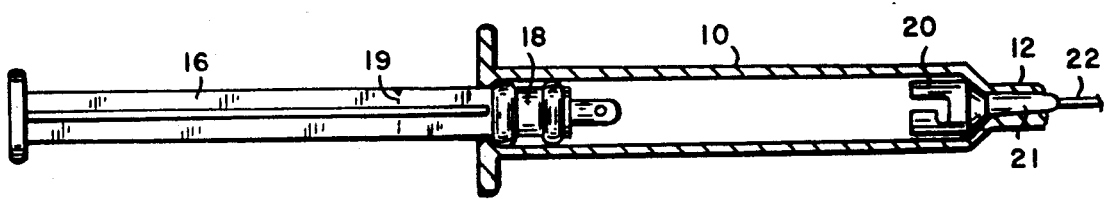
FIG. 3 is a partially cut away view of the syringe of the present invention, showing the detachment of the plunger assembly, e.g., for filling of the syringe with an injectable material.

FIG. 3 illustrates the typical positioning of the plunger assembly in the syringe after filling with an injectable solution (not shown). The vacuum seal created by gasket 18 and tips 12 and 21, allows the syringe to be filled with an injectable solution (not shown) as the plunger 16 is pulled back.

Figure 4:
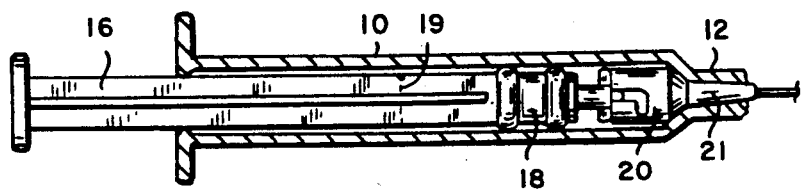
FIG. 4 is a partially cut away view of the syringe of the present invention, showing the positioning of the plunger assembly when an injection is being given (or has been given).

FIG. 4 illustrates the typical positioning of the plunger assembly as the contents of the syringe are being (or have been) injected. As illustrated, gasket 18 on the plunger assembly is preferably shaped in a configuration that creates a wiper effect in the barrel of the syringe, i.e., as it's drawn or pushed inside the barrel, thus maintaining an air tight seal, and ensuring both secure filling of the syringe, and as shown in FIG. 4, complete delivery of the syringe contents.

Figure 5:
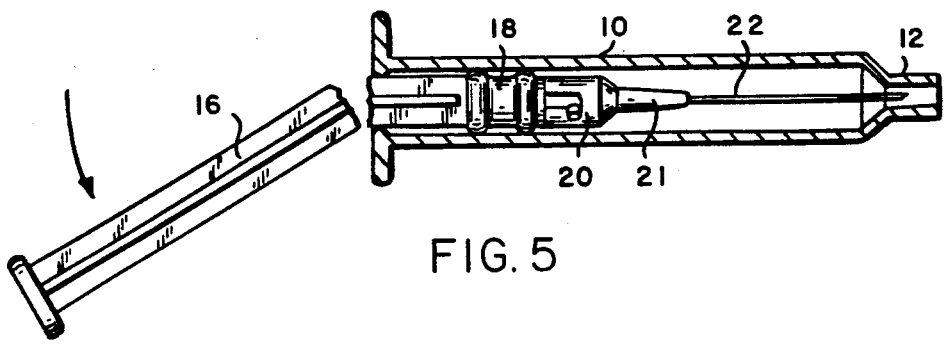
FIG. 5 is a partially cut away view of the syringe of the present invention, showing the positioning of the plunger assembly and the needle assembly after use, with the plunger assembly being broken off at the score line.

As illustrated in FIG. 5, after the syringe has been used to give an injection, the needle assembly is drawn back into the syringe barrel. This is accomplished by mating the male and female ¼-turn "T" members on the front end of the plunger assembly and on the back end of the needle assembly. For a close-up view of these assemblies, see FIG. 6. Once the needle assembly has been returned to the safe position within the syringe barrel, the plunger is withdrawn enough to expose score line 19. Once the score line on the plunger has been exposed at the back of the syringe, the plunger arm may be simply broken off. Advantageously, the score line is created during the molding of the plunger assembly, but it may be created by any means available to the skilled artisan.

FIG. 7 illustrates in cross-section, the wedge fit between tips 12 and 21 which assures that needle 22 will be held securely in a rigid state during both the filling of the syringe, as well (and most importantly) during the injection of the syringe contents into a patient. The wedge fit is sufficient to prevent the needle from being pushed back during use, but with a simple twist and pulling of the plunger, the needle may be retracted into the syringe barrel for safe disposal.

The components of the syringe of the present invention can be manufactured using any available material that meets the criteria of the invention. For commercial purposes, the manufacturing materials should be FDA approved. In other words, while injection molded plastics have been touted herein as a most convenient material for the syringe components, other commonly used syringe components can be adapted to benefit from the teachings of the present invention.

It will also be apparent to those having ordinary skill in this field, that any size syringe can be prepared according to the teachings of the present invention. Similarly, while the ¼-turn "T" type locking mechanism has been described herein as being convenient and simple, those artisans having ordinary skill in this field will recognize that other simple locking means can be employed herein, so long as they function in a manner consistent with the teachings of this invention.

While the present invention has been described in conjunction with the preferred specific embodiments thereof, it will be understood that the description is intended to illustrate and not limit the scope of the invention which is defined by the following claims.

What is claimed is:

1. A disposable safety syringe assembly comprising:
   (a) a substantially elongated barrel assembly, said barrel assembly having a forward end, a rearward end, an exterior surface and an Interior surface, with the interior surface defining an interior space, and wherein the barrel assembly is open ended in its rearward end, and wherein the forward end is provided with a constricted neck portion having a bore extending at least partially therethrough, and a needle breakable seal at the end thereof;
   (b) a backward and forward slidable needle assembly, disposed within said barrel assembly, said needle assembly including a substantially cylindrical hub member having a forward end and a rearward end, wherein the rearward end is provided with a locking member, and the forward end is provided with a constricted neck portion, said hub member further having a bore therethrough for communicating with the interior space of the barrel assembly; and wherein said constricted neck portion of said needle assembly is of a size and shape to removably wedge fit within the constricted neck portion of said barrel assembly, and wherein said needle assembly further includes a hollow needle mounted within the forward end of said hub member and passing through said constricted neck portion; and
   (c) a plunger assembly including a rod portion movable with respect to the syringe barrel assembly, said rod portion including a gasket member mounted on the rod near its forward end, and terminating with a locking member at its forward end, said locking member being capable of locking and unlocking with the locking member of the needle assembly;
   (d) wherein said locking member on said needle assembly consists of the female half of a ¼-turn "T" mechanism.

2. The disposable safety syringe assembly of claim 1, wherein said gasket member on said plunger assembly comprises a resilient material capable of engaging in a sealing frictional engagement with the inner wall of the syringe barrel assembly, and wherein said resilient material is slidable with respect thereto, thereby facilitating the drawing of liquid into said barrel upon retraction of said plunger and projection of said fluid from said barrel upon protraction of said plunger.

3. A disposable safety syringe assembly comprising:
   (a) a substantially elongated barrel assembly, said barrel assembly having a forward end, a rearward end, an exterior surface and an Interior surface, with the interior surface defining an interior space, and wherein the barrel assembly is open ended in its rearward end, and wherein the forward end is provided with a constricted neck portion having a bore extending at least partially therethrough, and a needle breakable seal at the end thereof;
   (b) a backward and forward slidable needle assembly, disposed within said barrel assembly, said needle assembly including a substantially cylindrical hub member having a forward end and a rearward end, wherein the rearward end is provided with a locking member, and the forward end is provided with a constricted neck portion, said hub member further having a bore therethrough for communicating with the interior space of the barrel assembly; and wherein said constricted neck portion of said needle assembly is of a size and shape to removably wedge fit within the constricted neck portion of said barrel assembly, and wherein said needle assembly further includes a hollow needle mounted within the forward end of said hub member and passing through said constricted neck portion; and
   (c) a plunger assembly including a rod portion movable with respect to the syringe barrel assembly, said rod portion including a gasket member mounted on the rod near its forward end, and terminating with a locking member at its forward end, said locking member being capable of locking and unlocking with the locking member of the needle assembly;

(d) wherein said locking member on said plunger assembly consists of the male half of a ¼-turn "T" mechanism.

4. The disposable safety syringe assembly of claim 1 or 3, wherein the locking members on said needle and plunger assemblies are adapted for repeated movement of locking and unlocking and when locked are capable of drawing said needle back into the syringe barrel assembly.

5. The disposable safety syringe assembly of claim 1 or 3, in which the syringe assembly is sealed in a sterile manner.

6. The disposable safety syringe assembly of claim 1 or 3, wherein the needle assembly has been pushed through the forward end of the barrel assembly, and locked therein by the friction between the two constricted tip portions, forming an interference or wedge fit.

7. The disposable safety syringe assembly of claim 1 or 3, wherein the barrel assembly includes a finger extension extending radially outward, said finger extension being positioned closer to said rearward end than to said forward end thereof.

8. The disposable safety syringe assembly of claim 1 or 3, wherein the plunger assembly includes a break-off means, located closer to said forward end than to said rearward end thereof, such that after withdrawal of the needle assembly into said barrel assembly, said plunger assembly may be broken off, rendering the syringe incapable of reuse.

9. The disposable safety syringe assembly of claim 8, wherein the plunger assembly has been broken off via the break-off means, and whereby the needle assembly is retained within the barrel assembly, such that the syringe is suitable for disposal.

10. A disposable safety syringe assembly consisting of:

(a) a substantially elongated barrel assembly, said barrel assembly having a forward end, a rearward end, an exterior surface and an interior surface, with the interior surface defining an interior space, and wherein the barrel assembly is open ended in its rearward end, and wherein is open ended in its rearward end, and wherein the forward end is provided with a constricted neck portion having a bore extending at least partially therethrough, and a needle breakable seal at the end thereof;

(b) a backward and forward slidable needle assembly, disposed within said barrel assembly, said needle assembly including a substantially cylindrical hub member having a forward end and a rearward end, wherein the rearward end is provided with a locking member, and the forward end is provided with a constricted neck portion, said hub member further having a bore therethrough for communicating with the interior space of the barrel assembly; wherein said constricted neck portion of said needle assembly is of a size and shape to removably wedge fit within the constricted neck portion of said barrel assembly, and wherein said needle assembly further includes a hollow needle mounted within the forward end of said hub member and passing through said constricted neck portion; and (c) a plunger assembly including a rod portion movable with respect to the syringe barrel assembly, said rod portion including a gasket member mounted on the rod near its forward end, and terminating with a locking member at its forward end, said locking member being capable of locking and unlocking with the locking member of the needle assembly;

(d) wherein said locking member on said needle assembly consists of the female half of a ¼-turn "T" mechanism.

11. A disposable safety syringe assembly consisting of:

(a) a substantially elongated barrel assembly, said barrel assembly having a forward end, a rearward end, an exterior surface and an interior surface, with the interior surface defining an interior space, and wherein the barrel assembly is open ended in its rearward end, and wherein the forward end is provided with a constricted neck portion having a bore extending at least partially therethrough, and a needle breakable seal at the end thereof;

(b) a backward and forward slidable needle assembly, disposed within said barrel assembly, said needle assembly including a substantially cylindrical hub member having a forward end and a rearward end, wherein the rearward end is provided with a locking member, and the forward end is provided with a constricted neck portion, said hub member further having a bore therethrough for communicating with the interior space of the barrel assembly; wherein said constricted neck portion of said needle assembly is of a size and shape to removable wedge fit within the constricted neck portion of said barrel assembly, and wherein said needle assembly further includes a hollow needle mounted within the forward end of said hub member and passing through said constricted neck portion; and (c) a plunger assembly including a rod portion movable with respect to the syringe barrel assembly, said rod portion including a gasket member mounted on the rod near its forward end, and terminating with a locking member at its forward end, said locking member being capable of locking and unlocking with the locking member of the needle assembly;

(d) wherein said locking member on said plunger assembly consists of the male half of a ¼-turn "T" mechanism.

12. The disposable safety syringe assembly of claim 10 or 11, wherein said gasket member on said plunger assembly consists of a resilient material capable of engaging in a sealing frictional engagement with the inner wall of the syringe barrel assembly, and wherein said resilient material is slidable with respect thereto, thereby facilitating the drawing of liquid into said barrel upon retraction of said plunger and projection of said fluid from said barrel upon protraction of said plunger.

13. The disposable safety syringe assembly of claim 10 or 11, wherein the locking members on said needle and plunger assemblies are adapted for repeated movement of locking and unlocking and when locked are capable of drawing said needle back into the syringe barrel assembly.

14. The disposable safety syringe assembly of claim 10 or 11, in which the syringe assembly is sealed in a sterile manner.

15. The disposable safety syringe assembly of claim 10 or 11, wherein the needle assembly has been pushed through the forward end of the barrel assembly, and locked therein by the friction between the two constricted tip portions, forming an interference or wedge fit.

16. The disposable safety syringe assembly of claim 10 or 11, wherein the barrel assembly includes a finger extension extending radially outward, said finger extension being positioned closer to said rearward end than to said forward end thereof.

17. The disposable safety syringe assembly of claim 10 or 11, wherein the plunger assembly includes a break-off means, located closer to said forward end than to said rearward end thereof, such that after withdrawal of the needle assembly into said barrel assembly, said plunger assembly may be broken off, rendering the syringe incapable of reuse.

* * * * *